(12) United States Patent
McGrath et al.

(10) Patent No.: US 7,306,601 B2
(45) Date of Patent: Dec. 11, 2007

(54) EXTERNAL FIXATION SYSTEM WITH PROVISIONAL BRACE

(75) Inventors: William M. McGrath, Colorado Springs, CO (US); Douglas N. Beaman, Hood River, OR (US); S. Robert Rozbruch, West Harrison, NY (US)

(73) Assignee: Quantum Medical Concepts, Inc., Portland, OR (US)

( * ) Notice: Subject to any disclaimer, the term of this patent is extended or adjusted under 35 U.S.C. 154(b) by 16 days.

(21) Appl. No.: 11/451,736

(22) Filed: Jun. 12, 2006

(65) Prior Publication Data

US 2007/0055234 A1   Mar. 8, 2007

Related U.S. Application Data

(60) Provisional application No. 60/689,357, filed on Jun. 10, 2005.

(51) Int. Cl.
*A61B 17/56* (2006.01)
(52) U.S. Cl. .......................................... 606/60; 606/61
(58) Field of Classification Search ............ 606/54–61, 606/72–73
See application file for complete search history.

(56) References Cited

U.S. PATENT DOCUMENTS

| | | | |
|---|---|---|---|
| 4,365,624 A | 12/1982 | Jaquet | |
| 4,768,524 A | 9/1988 | Hardy | |
| 4,784,125 A | 11/1988 | Monticelli et al. | |
| 4,889,111 A | 12/1989 | Ben-Dov | |
| 4,890,631 A | 1/1990 | Hardy | |
| 5,074,866 A | 12/1991 | Sherman et al. | |
| 5,358,504 A | 10/1994 | Paley et al. | |
| 5,702,389 A | 12/1997 | Taylor et al. | |
| 5,797,908 A * | 8/1998 | Meyers et al. | 606/54 |
| 5,885,282 A | 3/1999 | Szabo | |
| 5,919,192 A | 7/1999 | Shouts | |
| 6,030,386 A | 2/2000 | Taylor et al. | |
| 6,129,727 A | 10/2000 | Austin et al. | |
| 6,342,054 B1 * | 1/2002 | Mata | 606/59 |
| 6,428,540 B1 | 8/2002 | Claes et al. | |
| 6,701,174 B1 | 3/2004 | Krause et al. | |
| 6,702,814 B2 | 3/2004 | Walulik et al. | |
| 6,827,723 B2 | 12/2004 | Carson | |

* cited by examiner

*Primary Examiner*—Michael A. Brown
(74) *Attorney, Agent, or Firm*—Kolisch Hartwell, P.C.

(57) ABSTRACT

System, including methods and apparatus, for provisionally bracing an external fixator while the external fixator is reconfigured.

12 Claims, 6 Drawing Sheets

EXTERNAL FIXATION SYSTEM WITH PROVISIONAL BRACE

CROSS-REFERENCE TO RELATED APPLICATION

This application is based upon and claims the benefit under 35 U.S.C. § 119(e) of U.S. Provisional Patent Application Ser. No. 60/689,357, filed Jun. 10, 2005, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, fractured bones are treated using fixation devices, which reinforce the fractured bone and keep it aligned during healing. Fixation devices may take a variety of forms, including external fixators or casts for external fixation, and rods, bone plates, and/or fasteners (screws, pins, wires, etc.) for internal fixation, among others.

External fixators may utilize an adjustable frame disposed outside the body. The frame may be connected to and hold bone fragments at an adjustable spacing and angulation to create a desired overall bone length and angular disposition of the bone fragments. In some cases, the spacing and/or angulation may be changed over time via adjustments to the frame, to allow repair by progressive osteosynthesis between the bone fragments. Accordingly, external fixators may need to be reconfigured substantially after the frame has been installed; for example, frame components may need to be replaced with components of different size to enable sufficient expansion of the frame.

SUMMARY

The present teachings provide a system, including methods and apparatus, for provisionally bracing an external fixator while the external fixator is reconfigured.

DETAILED DESCRIPTION

The present teachings provide a system, including methods and apparatus, for provisionally bracing an external fixator while the external fixator is reconfigured. The methods may be used to replace one or more components, such as an adjustable strut(s), of an external fixator frame while the frame is connected to bone. The frame may be braced temporarily with a brace that stabilizes the frame while one or more frame components are replaced or adjusted, and then the brace may be removed while the frame remains in place. The brace may be adjustable between a movable configuration and a fixed/locked configuration, by hand, without the use of tools, and/or with one or more tools. Alternatively, or in addition, the brace may include a pair of clamps that engage frame members of the frame. Each clamp may define an opening for receiving a segment of a frame member. The clamp may be configured such that the opening is adjustable in size along a pair of orthogonal axes and/or may be biased toward opposing engagement with the frame segment. The clamp thus may be clipped onto the frame segment, positioned appropriately (for example, by sliding the clamp along the frame segment), and then locked in position by operation of a fastener mechanism that compresses the clamp. Overall, the present teachings may provide reconfiguration of external fixators that has one or more advantages over other approaches to reconfiguration, such as reconfiguration that is faster, easier, and/or less uncomfortable for the patient.

Further aspects of the present teachings are described in the following sections, including (I) overview of an exemplary fixation system with a provisional brace, (II) external fixators, (III) braces, (IV) methods of using braces for reconfiguration of external fixator frames, (V) kits, and (VI) examples.

I. Overview of an Exemplary Fixation System with a Provisional Brace

Figure 1:
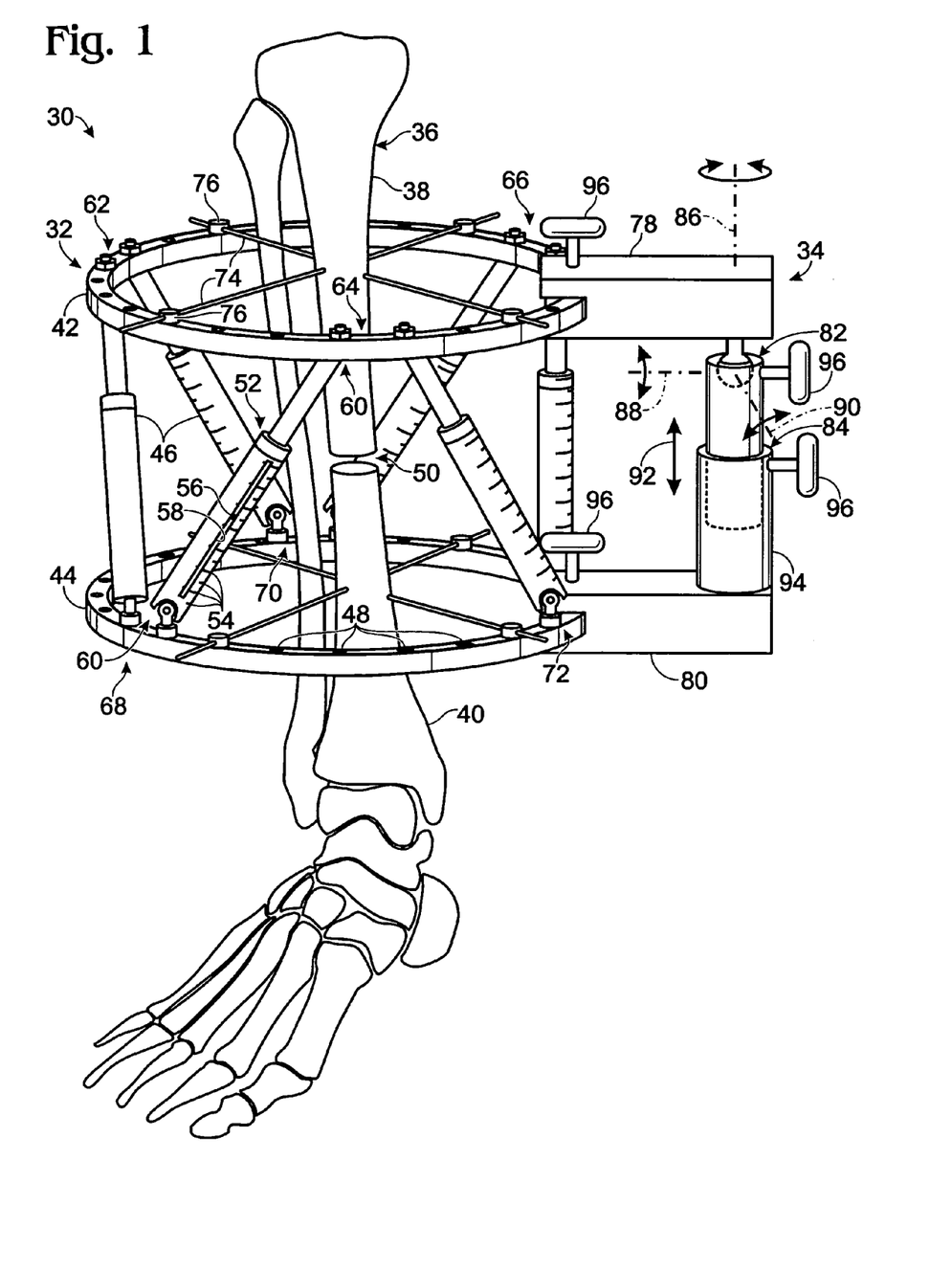
FIG. 1 is a view of an exemplary external fixation system connected to a tibia and including a provisional brace stabilizing a frame of the fixation system, in accordance with aspects of the present teachings.

FIG. 1 shows an exemplary external fixation system 30 including a frame 32 stabilized by a provisional brace 34. System 30 may be connected to a bone (or bones) 36, such as to bone fragments 38, 40 of a leg bone (the tibia) in the present illustration. Further aspects of suitable bones and orthopedic conditions for external fixation systems and braces are described elsewhere in the present teachings, e.g., below in Section IV, among others.

Frame 32 may include frame members 42, 44 connected to one another via struts 46. The struts may, for example, be received in openings 48 of the frame members that define potential (or actual) sites of strut attachment. Each frame member may be configured to extend at least partially or completely around bone, for example, the orthopedic rings shown here extend completely around the tibia. The frame members may be disposed adjacent respective bone fragments 38, 40 and thus generally opposing one another across a discontinuity 50 (e.g., a cut, break, or anatomical joint) in the bone(s). Each strut may be attached directly to frame members 42, 44 or may be attached indirectly, such as via fasteners and/or additional frame members of the frame (e.g., see Example 1 and FIG. 9).

The struts may determine the spacing and/or angular disposition of the frame members by holding the frame members in a substantially fixed relative disposition. Accordingly, each strut may be adjustable in length and/or angular disposition relative to the frame members or may have an adjustable site of attachment to a frame member along the strut, among others. In some embodiments, each strut may have an adjustment mechanism 52 that allows the length of the strut to be adjusted telescopically (and then fixed), and reference marks 54 and/or other indicia (e.g., alphanumeric characters) that allow a practitioner to read the length visually. For example, each strut may have an indicator 56 that slides along a channel 58 positioned adjacent the reference marks, to provide a measure of the strut length. Furthermore, each strut may have a pivotable joint(s) 60 disposed near each end of the strut, to permit the strut to pivot about at least one axis, but generally about a plurality of nonparallel (e.g., orthogonal) axes. Each strut thus may extend generally orthogonally to a plane defined by each frame member, at a fixed angle, or may be disposed obliquely to one or both planes at an adjustable angle, as shown here. In some examples, a plurality of struts (e.g., six) may be attached pairwise to a pair of frame members at spaced regions (e.g., three spaced regions) 62-72 around each frame member, to create a Taylor spatial frame, in which the various lengths of the struts collectively determine the fixed spacing and relative orientation of the frame members. Further aspects of frames are described elsewhere in the present teachings, e.g., below in Section II.

The frame members and thus the frame may be connected to bone via any suitable connectors. For example, the frame members may be anchored to bone with wires 74 that extend through bone between opposing sites of attachment on a frame member. The wires may be tensioned via wire clamps 76. Alternatively, or in addition, pins, rods, and/or screws, among others, may be used for connection of the frame to bone. However, in some examples, wires may have substantial advantages over other bone connection mechanisms, because the wires may permit repositioning of bone fragments relative to overlying soft tissue with relatively less damage to the soft tissue.

Brace 34 may be secured provisionally (temporarily) to the frame, to allow the frame to be reconfigured. Accordingly, the brace may include a pair of engagement elements 78, 80 that engage frame members 42, 44 tightly enough to restrict slippage of the engagement elements. The engagement elements may be received over the frame members, as shown here, and/or may be received through the frame members (e.g., see Example 2 and associated figures).

The brace may have a movable (adjustable) configuration, in which the spacing and/or angular disposition of the engagement elements is adjustable, and a fixed configuration in which the spacing and/or angular disposition is fixed. Accordingly, the brace may include one or more movable joints, such as at least one pivotable joint 82 and at least one translatable joint 84. The pivotable joint, which may be a single joint or a set of two or more joints with the same or different pivotal movement, may permit relative pivotal movement of the engagement elements about any suitable number of axes, such as orthogonal axes 86, 88, 90 shown here. The translatable joint may permit adjustment of the spacing between the engagement elements, indicated at 92, such as by a telescoping mechanism of a spanning portion 94 that connects the engagement elements. User controls (e.g., fasteners) 96 may be operated by hand (e.g., tightened or loosened by rotation), without the use of tools, and/or the brace may have user controls operated with tools, to change each joint and/or engagement element between its fixed (locked) and movable configurations. The ability of the brace to assume a range of lengths and internal angular dispositions permits the brace to engage the frame members disposed in a corresponding range of spacings and angular dispositions, and then to be fixed in position, to stabilize the frame members as the frame is reconfigured (e.g., as the struts are replaced and/or adjusted).

FIGS. 2-7 illustrate configurations of frame 32 and brace 34 produced before, during, and/or after performance of an exemplary method of reconfiguring the frame. Only selected portions of the frame and brace are shown here and in FIGS. 8-10.

Figure 2:
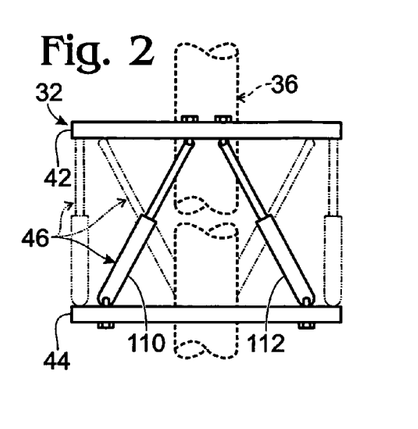
FIGS. 2-7 are elevation views of selected portions of the frame and/or brace of FIG. 1 in configurations produced before, during, and/or after performance of an exemplary method of reconfiguring the frame, in accordance with aspects of the present teachings.

FIG. 2 shows frame 32 connected to bone 36, with frame members 42, 44 held in a fixed relative position by struts 46. To simplify the presentation, bone 36 and the more rearward struts are shown in phantom. Moreover, to simplify the presentation further, frame members 42, 44 are shown oriented parallel to one another and perpendicular to the bone; in practice, frame members and bone may be oriented as shown or, more commonly, be tilted or angled relative to one another (including frame member relative to frame member). One or more of the struts may have been extended (or retracted) at least mostly (or completely) to their extension (or retraction) limit. Furthermore, a planned treatment plan for the bone (and thus the corresponding subject) may involve expanding (or retracting) the frame enough that the frame members would be repositioned beyond the extension (or retraction) limit of the struts. Accordingly, the one or more struts may need to be replaced with struts of a different size (e.g., with a greater maximum length or a lesser minimum length). In the present illustration, the front struts indicated at 110 and 112 are extended nearly maximally and thus need to be replaced to allow the frame to be expanded.

Figure 3:
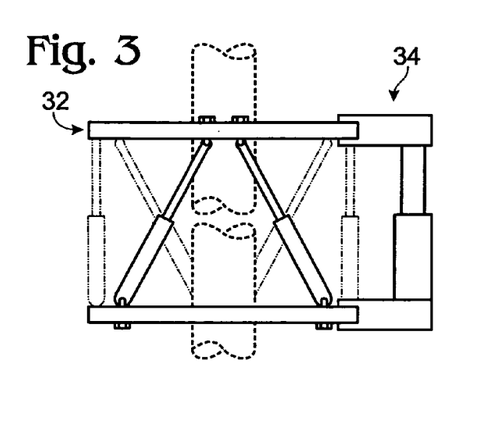

FIG. 3 shows frame 32 with brace 34 stabilizing the frame while all of the struts are still in position. The brace may be disposed at any suitable position around the frame relative to the struts to be replaced. For example, the brace may be positioned relatively near these struts, to improve stabilization when the struts are removed, or may be positioned relatively far from these struts around the frame, to provide better access to the struts. The brace may be placed into engagement with the frame members with the pivotable and/or translatable joints in a movable configuration, and then the joints may be locked (placed in a fixed configuration) to fix the relative dispositions of the frame members. Alternatively, any subset (or all) of the pivotable and/or translatable joints may be locked before the brace is engaged with the frame members.

Figure 4:
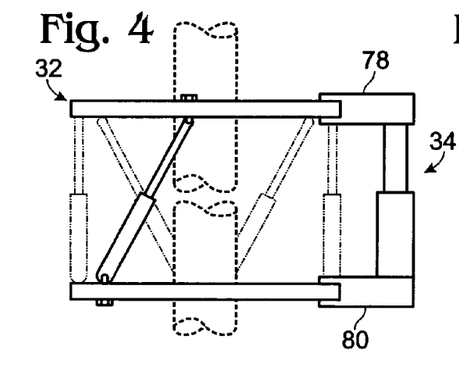

FIG. 4 shows frame 32 with brace 34 stabilizing the frame after front strut 112 (see FIG. 2) has been removed. Engagement elements 78, 80 of the brace may have a fixed relative disposition that restricts movement of the frame members. Without use of the brace, the frame may be substantially destabilized by removal of a strut and thus the frame members may undergo substantial undesired movement, which may be difficult and time-consuming to correct.

Figure 5:
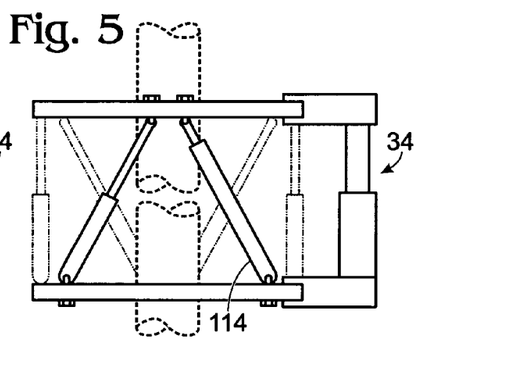

FIG. 5 shows the frame with brace 34 stabilizing the frame after one of the front struts has been replaced with a longer replacement strut 114. With the length of replacement strut 114 fixed (i.e., the strut locked), the brace may be removed if no additional struts are to be replaced during the same procedure.

Figure 6:
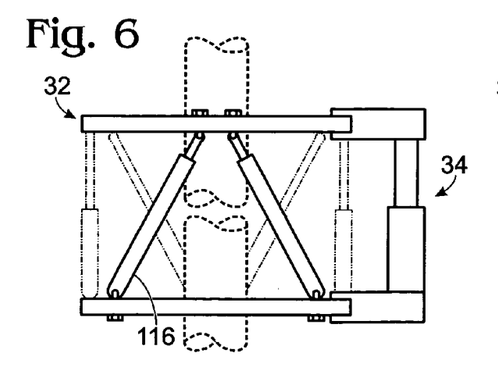

FIG. 6 shows frame 32 with brace 34 stabilizing the frame after the other front strut has been replaced with a longer replacement strut 116.

Figure 7:
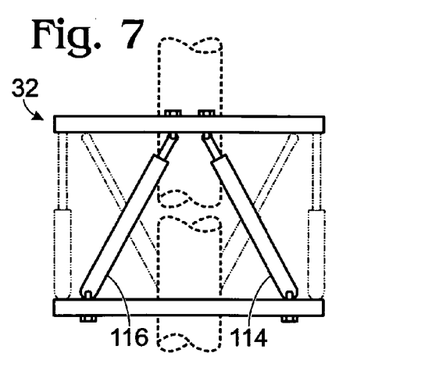

FIG. 7 shows frame 32 after the brace has been removed, with replacement struts 114, 116 and the other struts holding the frame members in place. Alternatively, one or more additional struts (or all of the struts) may be replaced before the brace is removed. Furthermore, the strut may be repositioned around the frame at any time that the frame is stable, for example, whenever a full set of struts is in place with their lengths fixed.

II. External Fixators

The systems of the present teachings involve bracing external fixators during their reconfiguration. An external fixator, as used herein, generally comprises any apparatus that connects to one or more bones and holds the bones in place from a position partially at least mostly outside the body. The external fixator may include a frame and connectors that extend from the frame to bone, to connect the frame to the bone.

A. Frames

The frame of an external fixator may include any framework of the fixator that is external to the body. The frame may have any suitable disposition relative to a bone(s). For example, the frame may extend along a bone(s) and/or partially or completely around the bone(s). Furthermore, portions of the frame that extend along and/or around the bone may be provided by the same or different frame components. In exemplary embodiments, the frame, which may comprise a Taylor spatial frame, includes (i) a plurality of frame members structured as discrete frame components, and (ii) a plurality of discrete struts that extend between and connect to (e.g., are secured to and/or in engagement with) at least a pair of the frame components.

i. Frame Members

The frame members, also termed base members or base components of the frame, may have any suitable shape. The frame members may be nonlinear or linear in overall shape. Nonlinear frame members may be curved, angular, or a combination thereof, among others. Furthermore, nonlinear frame members may be shaped to form an open or closed loop. For example, the frame members may be at least substantially circular or semicircular, corresponding to a full circle (e.g., a ring) or any suitable portion of a circle (e.g., an arc that is a quarter ring, a half ring, a three-quarters ring, etc.). Alternatively, the frame members may be elliptical, oval, parabolic, polygonal (e.g., rectangular), rosette, and/or a combination/portion thereof. The frame members may be generally planar, that is, extending along a two-dimensional path disposed in only one plane. Alternatively, the frame members also may bend out of the plane to follow a three-dimensional rather than a two-dimensional path. A fixator frame may have a plurality of frame members (or all frame members) with the same shape (e.g., a frame with two or more rings) and/or a plurality of frame members with different shapes (e.g., a frame with a full ring and a half ring).

The frame members may have any suitable sizes. In some examples, the frame members may be sized to extend at least partially (e.g., at least about half way) or completely around a bone (and overlying soft tissue and skin). Accordingly, some or all of the frame members of a frame may have a width or radius (particularly an inner width or inner radius) that is greater than the width or radius of a body region (e.g., a limb) that the frame members extend partially or completely around. For example, a frame member may be a ring with an inner radius defining a central opening large enough to receive a limb including a bone(s) to be fixed. The frame member may extend around a side(s) and/or an end(s) of a bone. The frame members of a frame may have the same or different overall widths or radiuses and the same or different local widths. The frame members also may have any suitable local width for segments disposed along each frame member. The local width along each frame member may be uniform or may vary, for example, to create tabs or other projections, and/or scallops, notches, or other recesses. Furthermore, the frame members may have any suitable thickness. The thickness may be uniform or may vary across and/or along a frame member (e.g., tapering inward or outward, or forming thinner and thicker regions along the frame member). The frame members of a frame may have the same or a different thickness.

Each frame member may include (or lack) one or a plurality of openings, to provide a perforated frame member. The openings may be, for example, through holes or blind holes, among others. The openings may be threaded or nonthreaded. Furthermore, the openings of each frame member may have a uniform size or may be of different sizes. The openings may be generally circular or may be elongate slots, among others. The openings may have any suitable arrangement and density in the frame member. For example, the openings may be equally spaced or may be more closely spaced in particular regions of the frame member.

The frame members may have any suitable construction and composition. Each frame member may be a single piece or may be formed or two or more pieces joined or connected otherwise to one another. The frame members may be formed of metal, plastic, a composite, and/or the like.

The frame members may be connected by any suitable number of struts. A strut, as used herein, is any support used to stiffen a frame, for example, restricting compression and/or distraction along a long axis of the strut. Each strut may have any suitable position and arrangement in a frame, generally extending between two (or more) frame members. The strut may have a fixed and/or adjustable length and/or angular disposition. Furthermore, if adjustable in length and/or angular disposition, the strut may be lockable (or not lockable) at a selected length and/or angular disposition ii. Struts A strut may have any suitable shape, size, and appearance. The strut may be elongate and substantially linear or may be bent (e.g., angular and/or curved). The strut may be a member of a set of struts of the same size and/or of different sizes. For example, the set of struts may include struts of the same and/or different diameter, the same and/or different maximum (and/or minimum) length, and/or the same and/or different angular adjustability. Distinct struts, of the same or different size/adjustability, may be marked as distinct. For example, the struts may include indicia, such as alphanumeric characters, distinct colors, removable (or permanent) colored bands, etc. In some examples, the struts of a frame may be marked to make them distinguishable, to facilitate keeping track of the various struts for introducing different adjustments to the struts over time.

A strut may include or lack one or more movable joints. Each movable joint may permit relative (internal) translational or pivotal motion of portions the strut. For example, the joint may permit pivotal motion about only one axis or a plurality of nonparallel axes. In some embodiments, the joint may permit twisting motion about an axis parallel to a long axis defined by the strut, and/or may permit a bending motion(s) about an axis (or axes) transverse to the long axis. The joint thus may be a hinge joint, a ball-and-socket joint, and/or a combination thereof, among others. The joint may have fixed and movable configurations and/or may be a nonfixable joint. In exemplary embodiments, the strut has a joint (or a set of joints) near each opposing end that permits pivotal motion about three orthogonal axes.

The struts may be secured to frame members by any suitable mechanism. For example, the struts and/or associated fasteners may extend through openings in the frame members and/or may extend partially or completely around each frame member, e.g., to engage each frame member via a clamp and/or a belt, among others.

iii. Taylor Spatial Frames

The frame members and struts collectively may create a Taylor spatial frame. A Taylor spatial frame, at used herein, is a framework including a pair of frame members connected by a set of struts, generally at least six struts, of adjustable length and angular disposition. In exemplary embodiments, the Taylor spatial frame has three pairs of struts connected to three spaced regions around each frame member, to define three points (and thus a plane) in which each frame member is disposed. The struts have an adjustable length and rotational freedom so that the spacing and angulation of the frame members can be adjusted by appropriate changes to the lengths of the struts. In some embodiments, appropriate strut adjustments may be calculated using a computer algorithm based on desired progressive changes to the spacing and/or alignment of associated bone fragments. Further aspects of Taylor spatial frames, including methods of using and adjusting the frames, are described in U.S. Pat. No. 5,702,389, U.S. Pat. No. 6,030,386, and U.S. Pat. No. 6,701,174, the disclosures of which are incorporated herein by reference.

B. Frame-to-Bone Connectors

An external fixator frame may be connected to bone by any suitable connectors. The connectors may extend into bone, through bone, and/or around bone, among others. Furthermore, the connectors may be slidably engaged with bone and/or fixed in relation to bone (e.g., threaded into bone). The connectors may extend from a frame member to bone, from a frame member to bone and then back to the same frame member (at a same of different (e.g., opposing) region of the frame member), and/or from a frame member to bone and then to a different frame member(s). Each frame member of a frame may be connected to bone via the same type of mechanism(s) as other frame members of the frame, may be connected by a different type of mechanism, and/or may be connected to bone only via another frame member of the frame.

The connectors may have any suitable structure. Suitable connectors may include wires, pins, rods, nails, plates, screws, bolts, staples, hooks, clamps, and/or a combination thereof, among others. In exemplary embodiments, the connectors may include wires that extend through bone, between opposing regions of a frame member.

III. Braces

The external fixation systems of the present teachings may include one or more braces used provisionally during frame reconfiguration. A brace, as used herein, generally includes any support that stabilizes or stiffens a frame as a frame is reconfigured (e.g., one or more struts of the frame is being replaced, adjusted, serviced, and/or installed).

The brace may include any suitable number of joints permitting any suitable internal relative motion of brace components (e.g., brace structures that engage frame members). Each joint may permit translational motion and/or pivotal motion of the brace components. In some examples, the brace may include one, two, or more joints that permit translational motion. Alternatively, or in addition, the brace may include one, two, three, four, or more joints that permit pivotal motion. Each pivotal joint may permit pivotal motion about only one axis (e.g., a hinge joint) or may permit pivotal motion about a plurality of axes, such as three orthogonal axes (e.g., a ball-and-socket joint). Accordingly, in some embodiments, the brace may have at least one, two, three, four, or more ball- and socket joints.

The brace may have any suitable user controls configured to permit a user to adjust the size, shape, and/or engagement of the brace. The user controls may be mechanical controls, such as knobs, wingnuts, levers, tabs, buttons, switches, bolts, nuts, screws, etc. The user controls may be operated manually, i.e., by direct engagement with a user's hand(s). Alternatively, or in addition, the user controls may be operated with a tool(s). The user controls may be, or may be connected to, fasteners. Furthermore, the user controls may be configured to be operated by any suitable motion, including rotational/pivotal motion and/or translational motion, among others.

The brace may include any suitable engagement elements for securing the brace to the frame. The brace may have any suitable number of engagement elements, such as two or more engagement elements. Each engagement element may be sized to engage one size of frame member or a plurality of different sizes of frame members. The engagement element thus may have a receiver structure that is adjustable over a continuous range and/or that has discrete, predefined positions at which the receiver structure can be set. The receiver structure may be adjustable along one axis or along a plurality of nonparallel axes, for receiving frame members of different local width and/or thickness. In some embodiments, the engagement element may include a clip structure that is biased toward a more closed position. Accordingly, the engagement element may be clipped onto a frame member and then held in place via the element's bias for opposing engagement with the frame member. In some examples, the bias may be sufficient to hold the engagement element in place during frame reconfiguration. Alternatively, or in addition, the engagement element may be locked to the frame member (with or without first clipping the engagement element onto the frame member) such that the engagement element is fixed in position.

The brace may include a clamp assembly of one or more clamps. The clamp assembly may mount on a pair of frame members to provide both a fixed and an adjustable connection between the frame members. In some examples, the clamp assembly may include at least a pair of clamps coupled to a spanning member that spaces the clamps. One or both clamps may be pivotably adjusted (and then fixed in position) about a plurality of nonparallel axis (e.g., three orthogonal axes) relative to the spanning member. Furthermore, one or both clamps may be translationally positioned (and then fixed) along the long axis of the spanning member and/or along one or more axes nonparallel to the long axis of the spanning member. In some examples, the clamp assembly may be configured to be adjusted, mounted, and fixed without the use of tools.

The clamp assembly may be used provisionally (or more permanently) as an aid to fracture reduction and/or frame reconfiguration. In particular, among other uses, the clamp assembly (or a plurality of clamp assemblies) may be used to stabilize a particular set of frame members temporarily, while the frame is reconfigured (and thus destabilized temporarily). For example, reconfiguration may involve replacement or repositioning of an associated strut (or plurality of struts). The brace then may be removed after frame reconfiguration, such that the reconfigured frame fixes bone without the brace. Moreover, this procedure may be repeated for the same or different sets of frame members and/or the same or different associated struts.

IV. Methods of Using Braces for Reconfiguration of External Fixator Frames

The systems of the present teachings include methods of reconfiguring an external fixator while the fixator is braced temporarily. The methods may include the following steps, performed in any suitable combination, performed in any suitable order, and with each step performed only once or a plurality of times. Further aspects of method steps that may be suitable and apparatus for performing the steps are described elsewhere in the present teachings.

The methods may be performed with a subject. The subject may be a human (a person) or another vertebrate animal.

One or more bones (of the subject) to be fixed may be selected. Any suitable bone(s) may be selected, such as a long bone(s) and/or at least a pair of bones connected via an anatomical joint. Exemplary bones include leg bones (femur, tibia, fibula), arm bones (humerus, radius, ulna), foot bones (tarsals, metatarsals, phalanges), wrist/hand bones (carpals, metacarpals, phalanges), etc. In exemplary embodiments, one or more bones including at least one long bone may be selected. The one or more bones selected may have any suitable orthopedic condition, such as a fracture, an osteotomy, a malunion, a nonunion, and/or a developmental defect (e.g., insufficient or excessive length and/or an undesired shape/angulation), among others. The orthopedic condition may be created, for example, by trauma, disease, a developmental defect, surgically, and/or a combination thereof.

A frame may be constructed along and at least partially around the selected bone(s). The frame may include a plurality of frame members fixed in position relative to one another by a plurality of struts secured to the frame members.

The frame may be connected to the selected bone(s). Connection may be performed at any suitable time, such as before, during, and/or after construction of the frame. For example, the frame may be assembled and then connected to bone, or individual frame members or frame sub-assemblies may be connected to the bone before the frame is fully assembled. Connection of the frame to bone may include placing connectors, such as wires, pins, screw, and/or rods, among others, through the skin and into, through, and/or around the selected bone.

The frame may be reconfigured while it is connected to the one or more selected bones. Reconfiguration may include adjusting the length, angle, position, and/or connection site of one or more frame components, particularly struts. In some embodiments, reconfiguration may involve lengthening and/or shortening one or more (or all) struts of the frame. In some embodiments, reconfiguration may involve replacing one or more struts with a different strut(s). The different strut may be of different size, pivotability, adjustability, shape, and/or the like.

The frame may be braced to facilitate reconfiguration. Bracing the frame may stiffen and/or stabilize the frame such that reconfiguration produces fewer undesired changes to the frame structure as the frame is weakened and altered during reconfiguration. Bracing may be performed by securing at least one brace to a pair of frame members of the frame. In some examples, the brace may be configured to be clipped onto the frame members before the brace is fully secured to the frame members. For example, the brace may include one or more frame engagement elements that are biased to opposingly engage one or more respective frame members. In any case, each engagement element may be secured in place on the frame member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the frame members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the frame.

The brace may be removed after frame reconfiguration. Accordingly, the brace may be installed with the frame (and connectors) fixing bone and removed with the frame reconfigured and still fixing bone. The brace thus may be present on the fixator frame for only a fraction of the time (e.g., less than about 10% or less than about 1% of the time) that the frame is fixing bone.

V. Kits

The fixation systems of the present teachings may include kits for external fixation of bones. The kits may include frame components for construction of a frame, such as at least a pair frame members (base components) and/or a plurality of struts. In some examples, the kits may include frame components for constructions of a Taylor spatial frame. The kits also or alternatively may include one or more braces for provisionally stabilizing the frame, bone connectors for connecting the frame to bone, a drill(s), a driver(s), a wire tensioner(s), instructions for use, a tray(s) for organizing and/or storing other components of the kit, and/or the like. These components may include any suitable aspects or features described elsewhere in the present teachings. Some or all of the components of each kit may be provided in a sterile condition, such as packaged in a sterile container. Furthermore, some of the components, such as bone connectors, may be configured for a single use, and others of the components, such as the brace(s), frame members, and/or struts, may be configured for repeated use.

VI. EXAMPLES

The following examples describe further aspects and embodiments of the present teachings, including exemplary braced configurations, exemplary frame components, and exemplary braces. These examples are included for illustration and are not intended to limit or define the entire scope of the present teachings.

Example 1

Exemplary Braced Configurations

Figure 8:
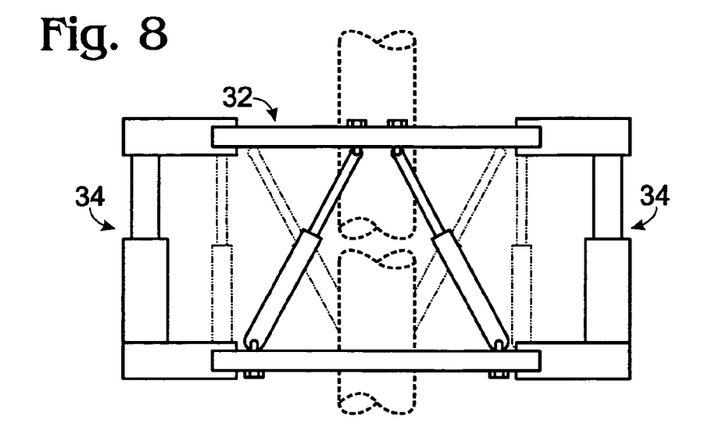
FIG. 8 is a somewhat schematic elevation view of the frame of FIG. 1 in an exemplary braced configuration using a plurality of the braces of FIG. 1, in accordance with aspects of the present teachings.
Figure 9:
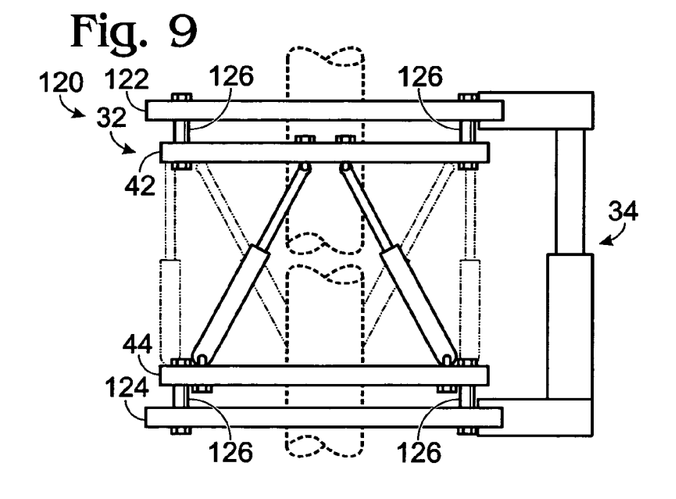
FIG. 9 is an elevation view of selected portions of another exemplary fixation frame being braced by the provisional brace of FIG. 1, in accordance with aspects of the present teachings.

This example describes exemplary braced configurations in which one or more braces stabilize a fixator frame; see FIGS. 8 and 9. Further aspects of fixator frames and methods of bracing fixator frames during frame reconfiguration are described elsewhere in the present teachings, for example, above in Sections I, II, and IV, among others.

FIG. 8 shows frame 32 in an exemplary braced configuration using a plurality of braces 34 at the same time. In some examples, stabilization with two or more braces may offer better stabilization than with one brace and/or may allow a greater number of struts to be replaced without moving the braces.

FIG. 9 show an exemplary composite fixator frame 120 being braced by brace 34. Frame 120 may be a composite structure created by core frame 32 with inner frame members 42, 44 (see FIG. 1) and one or more additional outer frame members 122, 124 flanking the core frame adjacent one other both ends of the core frame. Outer frame members 122, 124 may be connected to the core frame via, for example, orthogonal struts 126. The orthogonal struts may be rods that lack a pivotable joint. Alternatively, pivotable struts (e.g., see FIG. 1) may be used for connection of the outer frame members to the inner frame members (and thus to the core frame), such that the spacing and/or angular disposition of the core frame and the outer frame members is adjustable (and fixable).

Brace 34 may engage any suitable pair of the frame members connected by struts. For example, the brace may engage outer frame members 122, 124, as shown here. Alternatively, the brace may engage inner frame members 42, 44, or an inner and an outer frame member (such as frame members 122 and 42, 122 and 44, 42 and 124, or 44 and 124, among others).

Example 2

Exemplary Brace Connected Via Frame Openings

Figure 10:
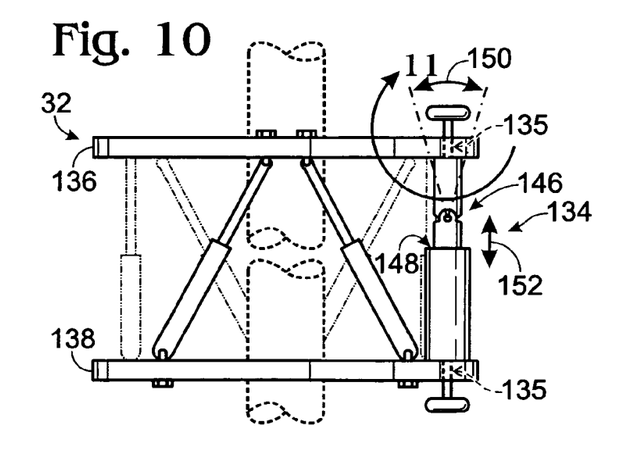
FIG. 10 is an elevation view of selected portions of the frame of FIG. 1 being braced by an exemplary brace connected via openings in frame members of the frame, in accordance with aspects of the present teachings.
Figure 11:
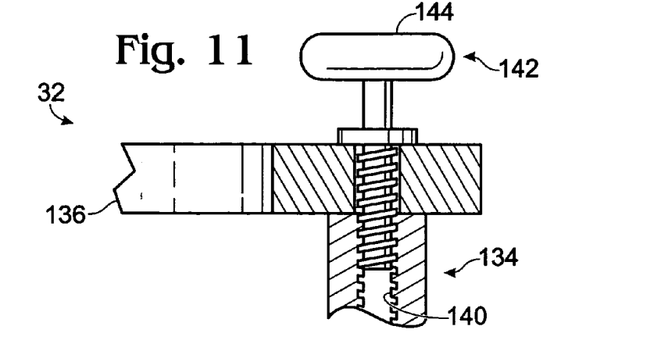
FIG. 11 is a sectional view of the frame and brace of FIG. 10, taken generally at "11" in FIG. 10.

This example describes an exemplary brace 134 that connects to a fixator frame 32 via openings 135 defined by frame members 136, 138; see FIGS. 10 and 11.

Brace 134 may have opposing ends that abut and/or extend through openings 135 of the frame members. For example, each end of the brace may have a threaded channel (or threaded exterior) 140 that receives a threaded fastener 142 (see FIG. 11). The threaded fastener may have a handle 144 for manual engagement and rotation and/or may be tightened or loosened with a tool.

Brace 134 may have a pivotable joint 146 and a translatable joint 148 (see FIG. 10). Each joint may have an adjustable configuration and a fixed configuration in which pivotal or translational motion, indicated at 150 and 152, is respectively permitted or restricted.

Example 3

Exemplary Frame Components

Figure 12:
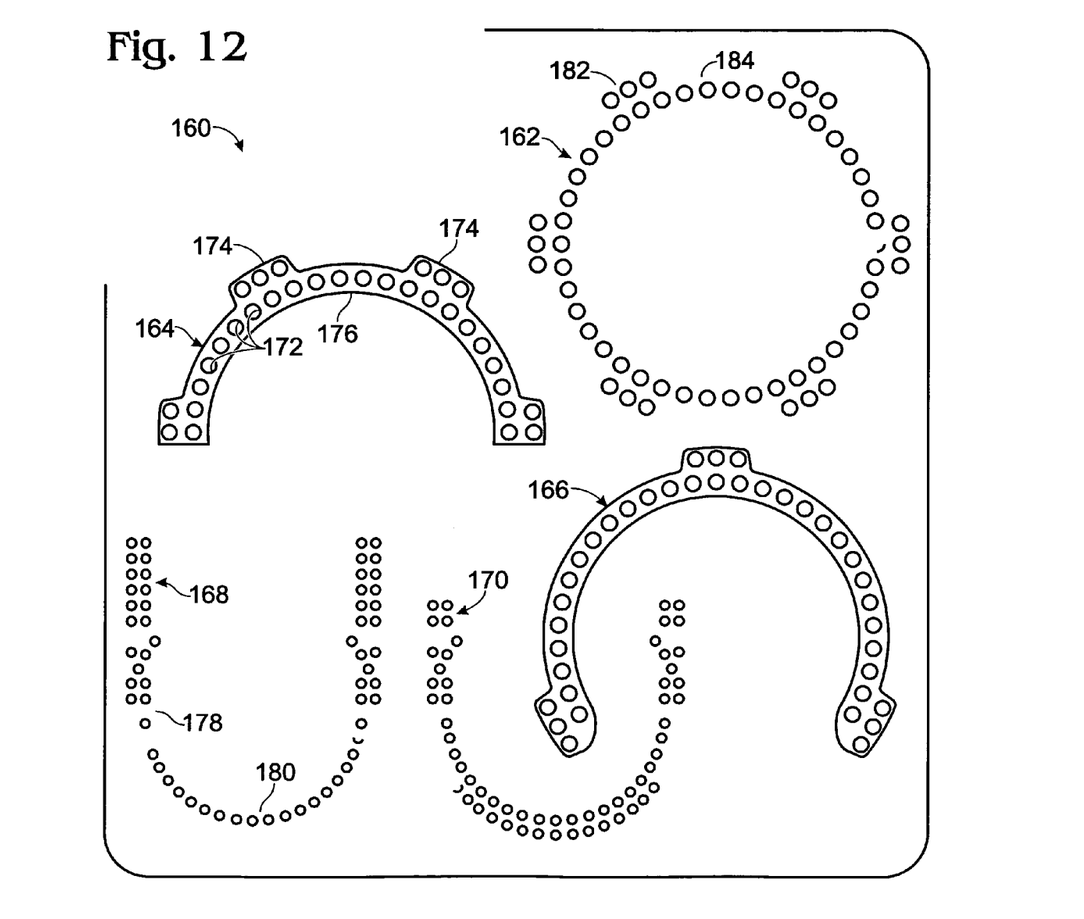
FIG. 12 is a plan view of a set of exemplary frame members that may be incorporated, in any suitable number and combination, into an exemplary fixator frame braced provisionally during frame reconfiguration, in accordance with aspects of the present teachings.

This example describes an exemplary set 160 of frame components for use in construction of an external fixator frame; see FIG. 12.

The set may include any suitable base components for a frame. The base components may be used any suitable number of times and in any suitable combination to construct a fixator frame. Exemplary base components may be structured as plates. The base components may include a full ring 162, partial rings (such as a half ring 164 and a three-quarter ring 166), and U-shaped plates 168, 170. Each base component may be perforated, with a plurality of through-holes 172 of any suitable size and arrangement. The base components may include tabs 174 that extend from a body 176 of each component. The tabs may extend, for example, from an inner or outer edge of the body and may be perforated. In some examples, the tabs may be suitable as attachment sites for struts. Braces of the present teachings may be configured to be received over a base component where there is no tab, in alignment with a tab, or both. Furthermore, braces of the present teachings may have a clamp mechanism defining an opening of adjustable size. Accordingly, the clamp mechanism may receive a base component at regions of different local width, for example, narrower region 178 and wider region 180 of plate 168 and/or tab region 182 and tab-free region 184 of full ring 162. Further aspects of base components (also termed frame members) are described elsewhere in the present teachings, for example, in Section II. Further aspects of an exemplary clamp mechanism capable of receiving base components of different local width are described elsewhere in the present teachings, for example, in Example 4.

Example 4

Exemplary Clamp-Based Brace

This example describes an exemplary brace structured as a clamp assembly; see FIGS. 13-16.

Figure 13:
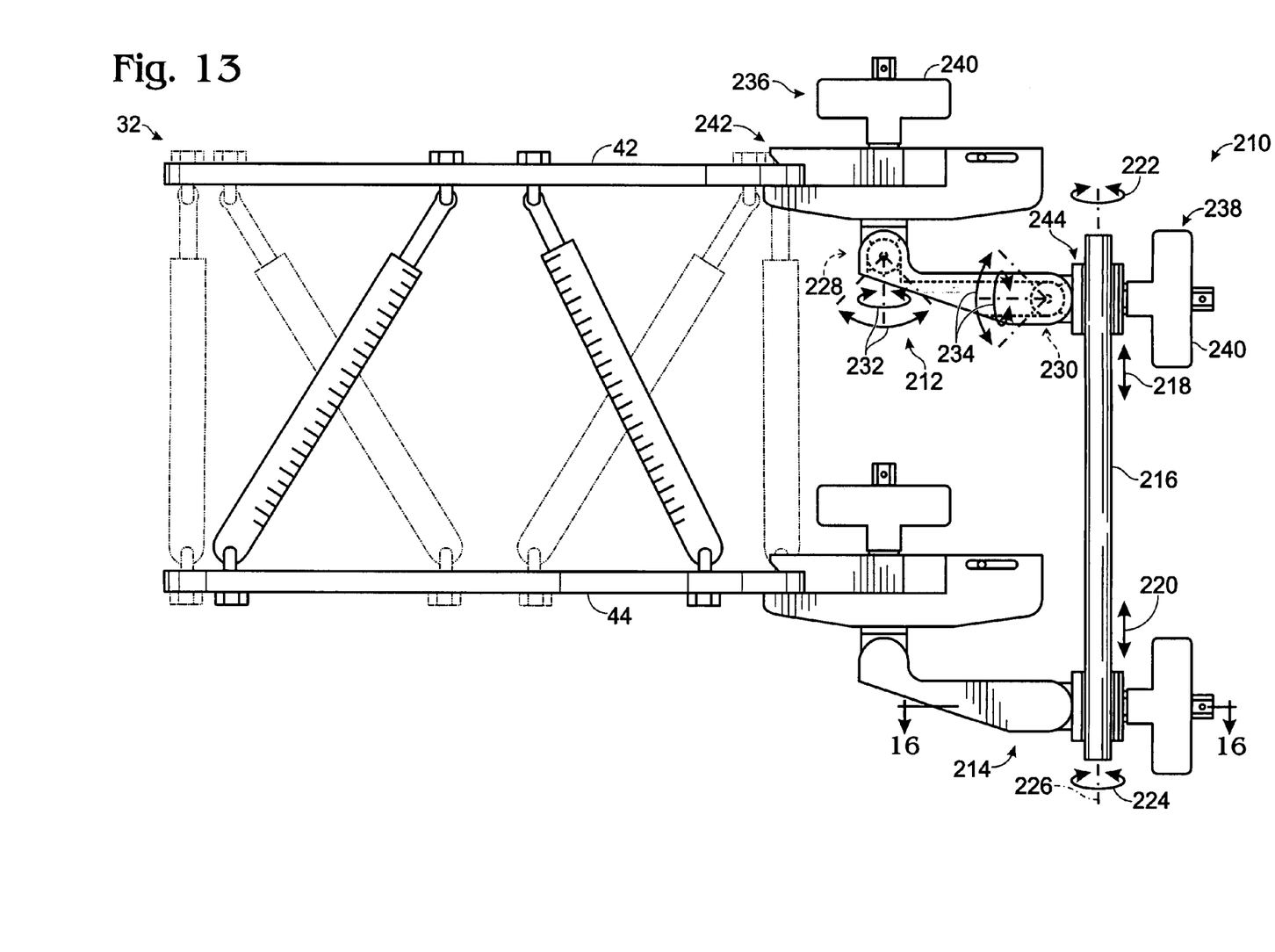
FIG. 13 is an elevation view of the frame of FIG. 1 stabilized with yet another exemplary brace, in accordance with aspects of the present teachings.

FIG. 13 shows selected portions of frame 32 (also see FIG. 1) stabilized provisionally with an exemplary clamp assembly 210. The frame may be stabilized by securing the clamp assembly to frame members 42, 44 of the frame and disposing the clamp assembly in a locked (fixed) configuration. The clamp assembly may include (1) a pair (or more) of clamp mechanisms 212, 214 that receive and opposingly engage the frame members, and (2) a spanning member 216 (such as a rod) connected to and extending between the clamp mechanisms. One or both clamp mechanisms may have three degrees of pivotal freedom and at least one degree of translational freedom relative to the spanning member. In the present illustration, the clamp mechanisms are of identical construction. However, in other examples, the clamp mechanisms may be structurally distinct.

Each clamp mechanism may be adjustably connected to the spanning member. For example, the clamp mechanism may be adjustable to accommodate translational motion along the spanning member, indicated respectively at 218 and 220. Accordingly, the clamp mechanisms may be fixed at selected positions along the spanning member to dispose the clamp mechanisms at a desired spacing from one another. Each clamp mechanism also may be fixed at a selected angular disposition relative to the spanning member by rotation of the clamp mechanism, indicated respectively at 222 and 224, about central long axis 226 of the spanning member.

Each clamp mechanism may have one or more pivotable joints capable of pivotal motion about one or more axes. For example, the clamp mechanism may have one or at least a pair of ball-and-socket joints 228, 230, each permitting a range of angular motion, indicated respectively at 232, 234, about three orthogonal axes. Each ball-and-socket joint may be loosened to a movable configuration, or tightened to a locked/fixed configuration, by manual (or tool-aided) adjustment of a respective fastener mechanism 236, 238. In particular, the fastener mechanism may be adjusted by engagement and rotation of a user control 240 (e.g., a handle or knob) that is connected to and/or part of the fastener mechanism. The clamp assembly thus may be very adjustable with a plurality of redundant degrees of pivotal freedom.

Each clamp mechanism may include one or more discrete clamps, particularly (1) a frame clamp 242 that engages and secures the clamp mechanism to a frame member of the frame (a ring in the present illustration), and/or (2) a connector clamp 244 that secures the clamp mechanism to the spanning member and thus creates a connection to the other clamp mechanism. Both the frame clamp and the connector clamp may be actuated and de-actuated (i.e., loosened and tightened relative to a frame member or spanning member) by user controls 240. Each user control also may be operatively coupled to the pivotable joints, for adjustment of the joints between pivotal and locked configurations.

Figures 14, 15:
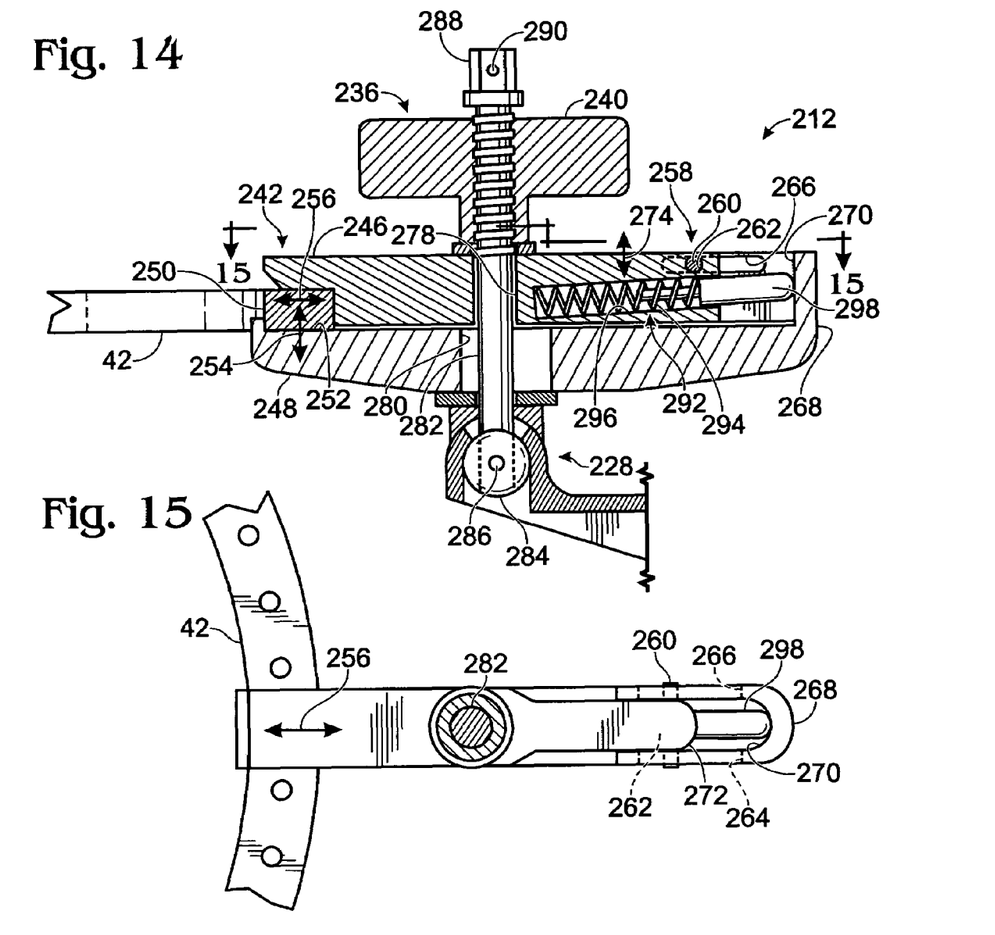
FIG. 14 is a sectional view taken through a clamp of the brace of FIG. 13.
FIG. 15 is a sectional view of the clamp of FIG. 14, taken generally along line 15-15 of FIG. 14.

FIG. 14 shows a fragmentary sectional view of clamp mechanism 212, particularly frame clamp 242. The frame clamp may include a pair of clamp elements or jaw elements 246, 248 (e.g., in the orientation show here, respective upper and lower jaws) configured to opposingly engage a transverse segment 250 of the frame member. The jaw elements may define a generally rectangular opening 252 that accepts a correspondingly shaped segment of the frame member. In particular, the jaw elements may engage the frame member opposingly along a single axis or along a pair of at least substantially orthogonal axes 254, 256. For example, in the present illustration, the jaw elements engage opposing upper and lower surfaces and also engage opposing inward and outward surfaces of the frame member. One or more jaw elements may include mating structure that matches or mates with corresponding mating structure on the frame, such as an opening in the frame. For example, upper jaw 246 may include a protuberance such as a pin that complements and can extend into an opening such as a hole in frame 42.

The jaw elements may be connected to one another by one or more suitable structures. For example, the jaw elements may be connected to one another by a pin-in-slot mechanism 258 and by fastener mechanism 236.

The pin-in-slot mechanism may be formed by a pin 260 received in aligned openings of the jaw elements. For example, upper jaw 246 may define a transverse bore 262, and lower jaw 248 may define a pair of opposing slots 264, 266 arranged laterally from one another and extending at least substantially parallel to a long axis of the lower jaw (see FIGS. 14 and 15). The slots may be defined by a U-shaped wall 268 projecting from a body of the lower jaw, to define a cavity 270 for slidably receiving a finger 272 of the upper jaw (see FIG. 15). The pin may permit and guide relative translational motion of the upper and lower jaws generally parallel to axis 256, to adjust the size of opening 252 in a dimension parallel to axis 256. Furthermore, the pin may permit relative pivotal motion, indicated at 274, of the upper and lower jaws about a pivot axis defined by the pin. The pivotal motion may permit adjustment of the spacing between the upper and lower jaws along axis 254, and thus adjustment of the size of opening 252 in a dimension parallel to axis 254. Accordingly, clamp 242 may define an opening that is adjustable in size along two orthogonal axes.

Fastener mechanism 236 also may connect the upper and lower jaws by extending through aligned openings 278, 280 of the jaws. One of the openings (e.g., opening 280) may be wider than the other, to permit one of the jaw elements (e.g., lower jaw 248) to slide along axis 256. Fastener mechanism 236 may include an externally threaded rod 282 received in openings 278, 280 of the jaw elements. Rod 282 may be attached to a ball 284 via a pin 286 adjacent a distal end region of the rod. The ball may be part of pivotable joint 228 and may restrict removal of the rod through openings 278, 280. Rod 282 may be disposed in threaded engagement with user control 240, which may be internally threaded and thus structured as an oversized nut. A proximal end region of rod 282 may have a cap 288 held in place with a pin 290. The cap may restrict the range of travel of nut 240, thereby preventing removal of the nut from the threaded rod. Rotation of the nut thus may determine the permitted spacing between the jaw elements along axis 254 (i.e., generally parallel to the adjustment axis defined by the fastener mechanism) and may be operative to provide a fixed relative position of the jaw elements along axis 256 by compression of the jaw elements around segment 250 of the frame member.

Frame clamp 242 also may include a biasing mechanism 292 connected to the jaw elements (see FIG. 14). The biasing mechanism may be configured to bias the jaw elements in relation to axis 256, for example, to urge the jaw elements together along axis 256, i.e., to decrease the size of opening 252 and thus urge the jaw elements into opposing engagement with the inward and outward surfaces of frame member 42. Accordingly, the clamp may be clipped onto a frame member, and held in place by the opposing engagement of the jaw elements until the jaw elements are locked in place by tightening the fastener mechanism. In some examples, the biasing mechanism also may bias the position of the jaw elements relative to one another along axis 254, for example, urging the jaw elements apart or together pivotally (and/or translationally).

The biasing mechanism may include a spring 294. The spring may, for example, be a coil spring received in a cavity 296 defined by the upper jaw. The spring may be engaged with a piston 298 that shields the spring from the exterior environment (see FIGS. 14 and 15). The cavity may be disposed generally parallel to a long axis of the upper jaw or skewed somewhat from parallel, as shown in the present illustration. A skewed or angled biasing mechanism may be suitable to bias the jaw elements along both of axes 254 and 256.

Figure 16:
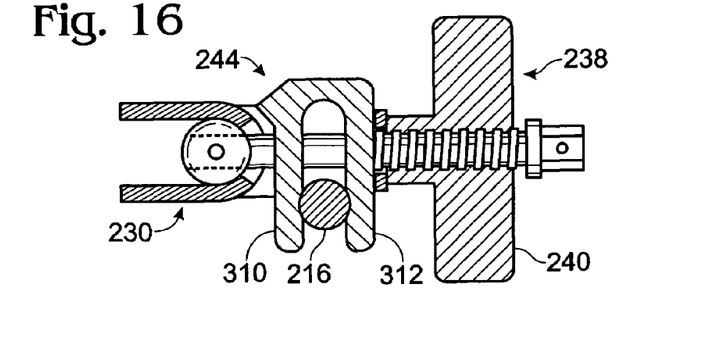
FIG. 16 is a sectional view of a movable joint of the brace of FIG. 13, taken generally along line 16-16 of FIG. 13.

FIG. 16 shows a sectional view of connector clamp 244 (see FIG. 13 also). The connector clamp may have jaw portions 310, 312 formed unitarily, as shown here, or by separate components. The jaw portions may adjustably engage spanning member 216 by adjustment of fastener mechanism 238, particularly by rotation of nut 240 in the present example. The fastener mechanism thus may control both pivotable joint 230 and connector clamp 244.

Example 5

Selected Aspects and Embodiments

This example describes selected aspects and embodiments of the present teachings, presented as a series of indexed paragraphs.

1. A system for treating an orthopedic condition, comprising: (A) a plurality of orthopedic rings; (B) one or more support members for spanning at least a pair of the orthopedic rings to stablize relative position of the pair of othopedic rings; and (C) a clamp assembly configured to be secured to the pair of orthopedic ring for provisional stabilization and/or adjustment of the relative position.

2. The system of paragraph 1, wherein the clamp assembly is configured to be secured and adjusted by hand, without the use of tools.

3. The system of paragraph 1, wherein the clamp assembly includes a pair of clamp mechanisms configured to be secured to respective members of the pair of orthopedic rings and also include a spanning member configured to extend between the pair of clamp mechanisms to define a spacing between the clamp mechanisms.

4. The system of paragraph 3, wherein at least one of the pair of clamp mechanisms is pivotable about three nonparallel axes relative to the spanning member.

5. The system of paragraph 4, wherein each of the pair of clamp mechanisms is pivotable about three nonparallel axes relative to the spanning member.

6. The system of paragraph 3, wherein at least one of the pair of clamp mechanisms is adjustble translationally relative to the spanning member along one or more nonparallel axes.

7. The system of paragraph 3, wherein at least one of the pair of clamp mechanisms has a pair of clamp members to create a jaw structure, and wherein the pair of clamp members are adjustable in relation to one another along at least two orthogonal axes.

8. The system of paragraph 7, wherein the at least one clamp mechanism includes a biasing structure configured to urge the clamp members together along the at least two orthogonal axes.

9. The system of paragraph 3, wherein at least one of the pair of clamp mechanisms has a pair of clamp members to create a jaw structure with a generally rectangular opening for receiving an othopedic ring, and wherein the rectangular opening is adjustable in width and length.

10. A clamp assembly according to the clamp assembly included in any of paragraphs 1-9, independent of the plurality of orthopedic rings.

11. A method of fixing bone, comprising: (A) selecting at least a pair of orthopedic rings coupled to bone; and (B) stabilizing a relative position of the pair of orthopedic rings with a clamp assembly configured to be secured to the pair of orthopedic ring.

12. The method of paragraph 11, wherein the step of stabilizing provides a relatively temporary stabilization of the pair of othopedic rings.

13. The method of paragraph 12, wherein the pair of orthopedic rings are connected by at least one strut, and wherein the step of stabilizing includes a step of attaching the clamp assembly to the pair of orthopedic rings, the method further comprising: (A) adjusting, after the step of attaching, at least one of the at least one struts, for example, to change the relative spacing and/or orientation of the pair of orthopedic rings; and (B) removing, after the step of adjusting, the clamp assembly from the pair of othopedic rings.

14. The method of paragraph 13, further comprising repeating the steps of attaching, adjusting, and removing for (A) the same and/or a different pair of rings, and/or (B) the same and/or a different at least one strut.

15. The method of paragraph 13 or 14, further comprising calculating an appropriate adjustment for the strut, prior to the step of adjusting.

16. The method of paragraph 15, wherein the struts include markings and/or other indicia that facilitate the calculation and/or the calculated adjustment(s).

17. The method of any of paragraphs 11-16, wherein the clamp assembly is according the clamp assembly of any of paragraphs 1-9.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, are also regarded as included within the subject matter of the inventions of the present disclosure.

We claim:

1. A method of reconfiguring an external fixator that is stabilizing bone, comprising:
    selecting a subject having one or more bones fixed by an external fixator including a frame having a pair of frame members adapted to be connected to the one or more bones and a plurality of struts defining a substantially fixed relative position of the pair of frame members;
    bracing the frame with a brace;
    reconfiguring the frame while the brace restricts movement of the pair of frame members; and
    removing the brace after the step of reconfiguring such that the external fixator with the reconfigured frame fixes the one or bones without the brace.

2. The method of claim 1, wherein the step of selecting a subject includes a step of selecting a subject with two or more of the plurality of struts extending obliquely relative to one another.

3. The method of claim 2, wherein the step of selecting a subject includes a step of selecting a subject having one or more bones fixed by a spatial frame that includes the plurality of struts.

4. The method of claim 1, wherein the step of selecting a subject includes a step of selecting a subject with each frame member extending at least about half way around a bone.

5. The method of claim 1, wherein the step of selecting a subject includes a step of selecting a subject with the pair of frame members secured to one or more bones via wires extending from the frame members and into the one or more bones, and wherein the step of bracing includes a step of engaging the pair of frame members with the brace.

6. The method of claim 1, wherein the brace includes a pair of clamps, and wherein the step of bracing includes a step of engaging the pair of frame members with the pair of clamps.

7. The method of claim 1, wherein the step of bracing includes (1) a step of adjusting at least one of a length and an internal angular disposition of the brace and (2) a step of securing the brace to the pair of frame members, and wherein the steps of adjusting and securing are performed by hand, without using tools.

8. The method of claim 1, wherein each of the plurality of struts has a length that is adjustable to an extension limit, further comprising a step of increasing the length of one or more of the plurality of struts to at least near the extension limit while the frame is connected to the one or more bones and before the step of bracing.

9. The method of claim 1, wherein the step of bracing includes (1) a step of clipping the brace onto a frame member, and (2) a step of locking the brace to the frame member after the step of clipping.

10. The method of claim 1, wherein the step of reconfiguring includes a step of replacing at least one of the struts with a replacement strut of different size while the brace restricts movement of the pair of frame members.

11. The method of claim 10, further comprising a step of repeating the step of replacing such that one or more others of the plurality of struts are replaced while the brace remains in the same position relative to the pair of frame members.

12. The method of claim 1, wherein the step of selecting a subject includes a step of selecting a subject having one or more bones fixed by an external fixator including a frame with two or more orthopedic rings as frame members.

\* \* \* \* \*